United States Patent [19]

Irie

[11] 3,948,725

[45] Apr. 6, 1976

[54] NEUTRAL PROTEASE USEFUL FOR ANIMAL TISSUE AND CELL CULTURE

[75] Inventor: Yoshio Irie, Matsudo, Japan

[73] Assignee: Godo Shusei Kabushiki Kaisha, Tokyo, Japan

[22] Filed: July 2, 1975

[21] Appl. No.: 592,534

Related U.S. Application Data

[62] Division of Ser. No. 474,771, May 30, 1974.

[52] U.S. Cl. ................................. 195/1.8; 195/1.7
[51] Int. Cl.² ......................................... C12K 9/00
[58] Field of Search ............. 195/1.7, 1.8, 4, 62, 65

[56] References Cited
UNITED STATES PATENTS
3,039,932    6/1962    McLimans et al. ................. 195/1.8

OTHER PUBLICATIONS

Keay, et al., Biotechnology and Bioengineering, Vol. 12, pp. 179–212 (1970).

Griffin, et al., Biochemical Journal, Dec. 1971, Vol. 125, No. 4, p. 109p.

Primary Examiner—Lionel M. Shapiro
Attorney, Agent, or Firm—Wenderoth, Lind & Ponack

[57] ABSTRACT

This invention relates to a neutral protease useful for animal tissue cell culture and having the chemical and physical properties disclosed in the body of the specification, characterized in that said protease is produced by aerobically culturing a strain of *Bacillus polymyxa* deposited at the American Type Culture Collection, Rockville, Md. under accession number ATCC 21993 on a culture medium containing a suitable carbon source and nitrogen source.

3 Claims, 9 Drawing Figures

NEUTRAL PROTEASE USEFUL FOR ANIMAL TISSUE AND CELL CULTURE

This is a division of application Ser. No. 474,771, filed May 30, 1974.

BACKGROUND OF THE INVENTION

This invention relates to a novel neutral protease produced by aerobically culturing a strain belonging to *Bacillus polymyxa*, preferably a strain of *Bacillus polymyxa* deposited at the American Type Culture Collection, Rockville, Md. under accession number ATCC 21993, and at the Fermentation Research Institute, Agency of Industry and Technology, Chiba City, Japan under accession number FERM-P-No. 412, on a culture medium containing a suitable carbon source and nitrogen source.

This novel neutral protease of the present invention is useful for animal tissue and cell culture, particularly in dispersing animal tissues, in dispersing animal tissue culture cells, and in suspension culture.

Heretofore, a method of tissue and cell culture has been developed in the field of research of the basic science and has been applied to the production of virus vaccine. It is considered that such method will become one of the most important techniques for the biological industry in future.

In the process of tissue and cell culture, it is a basic technique "to disperse tissue cells."

Prior to cultivating animal cells, the animal tissue should preferably be dispersed. After placing cells in a culture vessel, the tissue culture cells attached to the surface of the vessel are removed from the surface and dispersed to obtain a cell suspension. In order to cultivate on a large scale, it is convenient to cultivate animal tissue in a dispersed state, that is, to use a suspension culture process.

Heretofore in order to disperse tissue and cells, it has been attempted to add an enzyme or a chelating agent to a solvent for dispersion, or to mechanically disperse by means of scissors, spatulas, pipettes or the like. Rous and Jones used trypsin to disperse spleen tissue, tumertissue and the like of a fowl and a mammal. Medawar digested the heart tissue of a chicken embryo and human skin tissue by a tryspin solution, and successfully cultivated cells from the digested material. Dulbecco prepared a cell suspension by using a salty solution of tryspin in the process of monolayer culture of chicken embryo cells, and this culture was applied to his experiments on virus plaque formation.

Among conventional methods, Rappaport's and Bodian's methods are typical ones. Both methods use tryspin, but the former produces a cell suspension in a short time by using a relatively high temperature of 37° C to highly activate an enzyme which acts on the tissue employed, while the latter produces a cell suspension over a long time by using a low temperature (4° to 6° C) while stirring a solution containing tissue and an enzyme by means of a magnetic stirrer. Both methods provide cell suspensions which can be used for tissue culture.

Thus, tryspin was the main enzyme used for dispersing tissue and cells, but Rinaldini used pancreatin, elastase, papain and hyaluronidase in addition to trypsin in order to disperse the heart tissue of a fowl embryo, and found that elastase was useful in respect to digesting intercellular substances. Hinz et al used collagenase to culture human, pig and rabbit lungs. Hayashi et al made a comparative test of tryspin, pancreatin and the other various enzyme-containing compounds to digest human amnoin tissue and prepared suspended cells in a high yield by action of pancreatin for a short time. Gwatkin's et al used "Pronase" (trademark), which is a protease produced by streptomyces, to disperse mouse embryo tissue fragments, and obtained its monolayer culture.

Various enzymes and chelating agents have been studied for use in selectively cultivating a specific group of cells among various cells present in a tissue. Rappaport et al used boron tetraphenylate, which is a chelating agent for potassium, to disperse the liver of a mouse thereby obtaining hepatic parenchymal cells. Lasfarques prepared a group of epithelial cells by treating the mammary gland tissue of a mouse with bacterial collagenase for a long time thereby damaging cells of connective tissue.

However the above mentioned enzymes, except for "Pronase" and collagenase, are all derived from animal sources. Consequently, such enzymes are restricted in respect to their sources and it is complicated to prepare them. Therefore they are rather expensive. In addition to the above general disadvantages, tryspin has many other defects in that it is inhibited by serum; that its optimum pH range of activity is relatively narrow (pH 7.2 to 7.4); that it is rapidly inactivated by incubation; that it tends to damage the cells on a certain concentration of tryspin; and accordingly that very careful operation is required. Animal tissues to which collagenase is applied are restricted since the collagenase works only with tissues containing collagen. There is a risk that crude enzymes derived from an animal source include mycoplasm. "Pronase" has disadvantages in that it is often heterogenous in quality and accordingly that reproducibility is unfavorable. According to Gwatkin's operating conditions, cells are highly apt to be damaged. In view of the above mentioned disadvantages in the prior art, an enzyme which has none of the above disadvantages and which can be easily handled, is desired.

DESCRIPTION OF THE INVENTION

The enzyme of the present invention is a neutral protease produced by bacteria and overcomes the above mentioned defects. A neutral protease can be produced by various bacteria, but this invention relates particularly to the protease which is produced by a strain of *Bacillus polymyxa* deposited at American Type Culture Collection under accession number ATCC 21993 (and also deposited under the Japanese Fermentation Research Institute Agency of Industry and Technology under accession number FERM-P-No. 412). carbohydrate, The protease of this invention is produced by carrying out a liquid culture for 2 to 7 days at pH 5 to 8 uncer a temperature of 20° to 37° C on a synthetic medium or a natural medium containing a suitable amount of carbohydrate, a nitrogen source and inorganic salts respectively. Any method of surface culture, shaken culture or culture under aeration can be employed, but shaken culture and culture under aeration are generally preferred.

After the completion of the culture, the bacterial cells are removed and the protease solution is obtained. The thus obtained protease solution is subjected to a purification operation such as salting out, precipitation by solvent, concentration under reduced pressure and the like to obtain a concentrated protease solution. Most of the active protease is precipitated by salting out the concentrated protease solution with 60 to 80% saturated ammonium sulfate solution. The precipitation can also be carried out with 75% methanol, 70% ethanol, 60% acetone or 70% isopropanol, the yield of the active protease being 88%, 80%, 70% and 75% respectively. The crude protease thus obtained can be preserved in quite a stable state at pH 4 – 9 under a temperature of 5° C for 7 days, and it can be similarly preserved at 27° C for 24 hours.

The protease of the present invention has the following chemical and physical properties, and was found to be a novel protease.

a. Function

The protease of this invention functions as a neutral protease.

b. Specificity to substrate

This protease has a mild proteolytic activity to casein.

c. Optimum pH value and stable pH range

Optimum pH: The optimum pH for proteolytic activity to casein is 8.5.

Stable pH range: This protease is very stable within the pH range of 4.0 to 9.0.

d. Assay method of activity

The activity is expressed in units of hemoglobin in accordance with Anson's Method.

e. Active temperature range

This protease is active within the temperature range of 20° to 75° C. The optimum temperature is 60° C.

f. Enactivation by pH and temperature

The activity is completely lost at a pH of below 3.0 and at a pH of above 10.0. The activity is also completely lost by heating at 65° C for 10 minutes.

g. Inhibition and activation

The activity is inhibited by metal-chelating agents such as ethylenediaminetetraacetate (EDTA), citric acid, o-phenanthroline, 2,2'-dipyridyl and sodium fluoride, and oxidizing agents such as N-bromosuccinimide (NBS) and iodine. The activity is enhanced by the addition of metallic ions such as $Ca^{++}$, $Mn^{++}$, $Mg^{++}$, $Fe^{++}$, $Fe^{+++}$ and $Al^{+++}$.

h. Method of purification

The crude protease of the present invention is crystallized by the following procedure.

The crude protease is dissolved in M/500 calcium acetate solution, and the insoluble material is removed by filtration or centrifuge. Ammonium sulfate is added to the filtrate to make a 40% saturated solution, and the precipitated material (nonactive fraction) is removed by filtration or centrifuging. Further ammonium sulfate is added to the resultant filtrate to make a 70% saturated solution, and the precipitated material is recovered by filtration or centrifuging. The precipitated material thus obtained (which is precipitated from 70% saturated ammonium sulfate solution) is dissolved in M/500 calcium acetate solution, and the resultant solution is subjected to dialysis in a cellophane tube or bladder membrane against M/500 calcium acetate solution.

The cellophane tube or bladder membrane permits passage of ammonium sulfate but not the protease of this invention. The dialysis is carried out at 5° C, and after 3 days the inside solution in the semi-permeable membrane begins to crystallize. After 7 days, the crystallized material is recovered by centrifuging. The crystallized material thus obtained is mixed with M/500 calcium acetate solution to form a suspension, and is dissolved by adding dilute NaOH solution dropwise at a low temperature. Immediately after the addition of the NaOH solution, dilute HCl solution is added to make the pH value of the solution 8.0, and the insoluble material is removed by centrifuging. The pH value of the solution is then made 6.8 The resultant solution is allowed to stand at a low temperature to crystallize out the protease of the present invention.

i. Molecular weight:

In accordance with ultracentrifugal analysis, the molecular weight of the protease of this invention was determined to be 35,900.

j. Crystal structure

The crystal structure of the protease has not been fully determined, but the crystal obtained in accordance with the purification method of Item (h) was stick-like or needle-like.

k. Elemental analysis

The elemental analysis of the crystal obtained in accordance with the purification method of Item (h) was as follows:

C: 46.57%, H: 7.17%, O: 31.57%, N: 14.48%, and S: 0.21%

The protease of this invention was found to attack peptide bonds in the "oxidized B-chain" of insulin at the following 12 positions: Phe(1)-Val(2), His(5)-Leu(6), His(10)-Leu(11), Glu(13)-Ala(14), Ala(14)-Leu(15), Leu(15)-Tyr(16), Tyr(16)-Leu(17), Leu(17)-Val(18), Gly(23)-Phe(24), Phe(24)-Phe(25), Phe(25)-Tyr(26) and Lys(29)-Ala(30)

In addition to the above properties, the neutral protease of this invention has the following characteristics in comparison with trypsin which has been used heretofore to disperse tissue and prepare a cell-suspension.

Tryspin effectively digests tissues in the absence of serum, calcium and magnesium ions. Serum contains tryspin inhibitors. Consequently, it is impossible to use an ordinary culture medium containing serum, for tryspin treatment. However culture mediums not containing serum, calcium and/or magnesium ions are unsuitable for cells since the cells are damaged in such culture mediums. On the other hand the activity of the neutral protease of this invention is not substantially inhibited by serum, calcium and/or magnesium, and accordingly the neutral protease of this invention can work regardless of the inclusion of these components. Further it is possible to easily stop the activity of protease by diluting the protease solution without affecting the lives of the cells. When trypsin is employed to disperse a tissue, the working conditions such as treating time, enzyme concentration and the like are narrowly restricted, while the working conditions of the neutral protease of this invention are generally broad and cells are not easily damaged even if the working conditions extend outside the particular treating time and concentration ranges. From these aspects, it is clear that the neutral protease of this invention works more conveniently and effectively than trypsin in dispersing tissues of various organs to prepare tissue cultures from them and in dispersing tissue culture cells attached to the surface of the culture vessel and growing thereon.

The protease of this invention is further characterized in that its activity is maintained for a long time when it is kept at " C. Owing to this characteristic, it has become possible to carry out a suspension culture by adding the protease of this invention to a culture medium. Heretofore, a suspension culture could be carried out only when a particular type of strain was employed, and it was necessary to apply a mechanical force such as stirring to the culture medium in order to strip off cells attached to the surface of the culture vessel. Sometimes it was necessary to add a viscous material and a surface active agent in order to facilitate the dispersion of cells and to prevent their coagulation. An attempt was made to employ trypsin to facilitate the dispersion of cells and to carry out a suspension culture, but tryspin was inhibited by the protein in serum and its activity was rapidly lost at the temperature employed for the culture. This, trypsin can be employed only under very limited conditions, that is, only for a suspension culture using a medium containing non-serum. On the other hand, the protease of this invention is not inhibited by serum and does not damage cells. Moreover the activity of the protease of this invention is maintained for a long time at the temperature employed for the culture. In a culture medium containing the protease of this invention, cells grow in the state of dispersion, and it is possible to carry out a suspension culture using an ordinary culture medium without employing a viscous material and a surface active agent.

BRIEF DESCRIPTION OF THE DRAWINGS

FIG. 6-1 is a phase contrast micrograph (x 240) of L-929 cells obtained by a stationary suspension culture at 37° C for 2 days in MEM-FCS (9 : 1) solution containing the protease of this invention at a concentration of 200 u/ml.

FIG. 6-2 is a phase contrast micrograph (x 240) of L-929 cells obtained by a stationary suspension culture at 37° C for 2 days in MEM-FCS (9 : 1) solution containing no protease.

DESCRIPTION OF THE PREFERRED EMBODIMENT

The following Examples illustrate a method of preparing the protease of this invention, a method of dispersing animal tissue, a method of dispersing tissue culture cells and a method of suspension culture, which respectively use the neutral protease of this invention.

PREPARATION EXAMPLE

Preparation of the protease of this invention

100 L of a medium containing 40% of defatted soybean cake extract which was obtained from 5% of soybean flake in dilute alkaline solution and was digested with alkaline protease, 0.5% of corn steep liquor, 3.5% of glucose, and 1/100 M $CaCl_2$ was inoculated with a strain of *Bacillus polymyxa* ATCC 21993 (or FERM-P No. 412).

After 40 hours' submerged culture in 200 L fermenter at 30° C (aeration 100 L/min, agitation 200 rpm.), the proteolytic activity of the broth reached its maximum, 4000 unit/ml.

The cells and insoluble fraction of the broth were removed by gel-filtration, and the filtrate was concentrated under reduced pressure. After fractionation by isopropanol (35 – 70%), 700 grams of the enzyme of this invention was obtained, and its specific activity was 428,000 unit/g. The recovery of the activity was found to be 70%.

EXAMPLE 1:

Dispersion of the heart tissue of a chicken embryo and its primary culture

The heart of a 10-days incubated chicken embryo was cut in two with a scalpel, and each piece was put in a dish. Each piece was cut into smaller pieces, and the cut pieces were dispersed in 1 ml of the respective protease solutions disclosed in the following Table 1. Each of the resultant solutions was put in a test tube, and kept at 37° C for 30 minutes. After incubation, 4 ml of a mixed culture medium prepared by mixing Eagle's minimum essential medium (hereinafter referred to as MEM) with foetal calf serum (hereinafter referred to as FCS) in a ratio of 9 to 1 were added and mixed with a pipette thereby forming a suspension of free cells. The resultant mixture was allowed to stand for 1 minute to deposit small tissue pieces. The supernant suspension of cells was put in another test tube, and was subjected to a centrifuge for 10 minutes at 700 rpm thereby depositing cells. The supernant liquid was discarded and the deposited cells were dispersed in 4 ml of a mixed culture medium comprising F 12 medium of Ham (hereinafter refers to as F 12), MEM and FCS in a ratio of 4.5 : 4.5 : 1. The resultant dispersion was placed in a glass dish having a diameter of 5 cm and was subjected to a stationary culture at 37° C for 2 days in a humidifier atmosphere containing 5% carbon dioxide in air. On the other hand, the small tissue pieces left in the first test tube were mixed with 4 ml of the same mixed culture medium as above and placed in a glass dish and the mixture was subjected to a stationary culture in the same manner as above.

After the cultivation, the medium was discarded, and the cells were fixed with 70% ethanol as they were, without stripping the cells off the glass surface of the culture vessel, and were dyed with crystal violet solution.

As a method for the evaluation of the results, the culture in which the dispersed cells formed a mono-layer was marked as ++, and the culture in which the cells did not form a mono-layer but attached to the glass surface of the culture vessel was marked as +. Further, the culture in which tissue pieces were dispersed and cells grew over the glass surface from the tissue pieces was marked as ++. The culture in which tissue pieces were coagulated and cells did not grow on the glass surface so much was marked as +.

The amount of free cells obtained by treating the tissue with the protease of this invention in each of the MEM-FCS solution and phosphate buffer salt solution (hereinafter referred to as PBS) was substantially the same as that obtained by treating the same tissue with tryspin in PBS. When the tissue was treated with trypsin in PBS, a viscous coagulation of tissue pieces was formed, but, it is heretofore known that such a viscous coagulation of tissue pieces is caused by damaging the cells. However, when the tissue is treated with the protease of this invention in a serum-containing medium, such a coagulation as seen in the treatment by tryspin did not appear and many cells from the treated tissue pieces grew over the glass surface (see Table 1).

A very similar result was obtained when the same test was carried out using the heart of a rat embryo in place of the heart of a chicken embryo.

In conclusion, it has been found that the protease of this invention works to disperse tissue in a serum-containing medium to the same extent as the dispersion of the tissue in PBS solution by trypsin, and the damage to the cells can be kept to a minimum by the use of the protease of this invention.

Table 1

Primary culture of the heart tissue of a chicken embryo dispersed by protease of this invention and trypsin

| | Culturing condition | | Evaluation | |
|---|---|---|---|---|
| | Enzyme | unit/ml | Culture medium | Culture of dispersed cells | Culture of tissue pieces |
| 1 | Protease of this invention | 1000u | MEM-FCS (9 : 1) | + | ++ |
| 2 | " | 2000u | " | ++ | ++ |
| 3 | " | 1000u | PBS | + | + |
| 4 | " | 2000u | " | ++ | + |
| 5 | trypsin | 1000u | " | + | + |
| 6 | " | 2000u | " | ++ | + |
| 7 | " | 1000u | MEM-FCS (9 : 1) | − | − |
| 8 | " | 2000u | " | − | − |

The evaluatioin (-) means that it is impossible to carry out culture by using trypsin when MEM-FCS is employed as a culture medium since the trypsin is inhibited by serum in the MEM-FCS culture medium.

EXAMPLE 2:

Dispersion of the body of a chicken embryo and its primary culture and successive culture Seven bodies of 11-days incubated chicken embryos from which the internal organs, heads and legs were removed were injected through a syringe. To 10 ml of the injected tissue pieces, were added 50 ml of a phosphate buffer salt solution containing calcium and magnesium ions (Dulbecco's PBS). The resultant mixture was fully stirred and 10 ml of the mixture were poured into each of five conical flasks. To each of the conical flasks containing the tissue pieces, were added 10 ml each of protease solutions prepared by dissolving the protease of this invention or trypsin in Dulbecco's PBS, the concentration of which is disclosed in the following Table 2-1. The contents of the conical flask were kept at 37° C for 30 minutes, and the resultant protease solution containing tissue pieces and suspended viable cells was then filtered through a 150-mesh stainless steel sieve. The filtrate was subjected to a centrifuge at 1,000 rpm for 5 minutes to separate cells from the protease solution. The cells thus obtained were dispersed in a mixed culture medium comprising MEM, Tryptose phosphate (Difco) and calf serum in a ratio of 9 : 0.5 : 0.5 (hereinafter referred to as MEM-TPB-CS) to prepare a cell suspension. The number of viable cells in the cell suspension was measured by means of the erythrosine staining method (see Table 2-1).

In the primary culture 5 ml each of the MEM-TPB-CS solution containing 5 × 10$^6$ cells obtained by the treatment with the respective protease solutions were placed in a plastic dish having a diameter of 5 cm, which was then kept at 37° C for 4 days in a humidified atmosphere containing 5% carbon dioxide in air. Subsequently the medium was discarded from each of the solutions, and the protease solutions disclosed in Table 2-2 were added to the remaining cells respectively. The resultant solutions were incubated and cells attached to the surface of the dish were stripped off to form a cell suspension. The number of viable cells in the cell suspension was measured by means of the erythrosine staining method (see Table 2-2).

In carrying out successive culture, 5 ml of cell suspension containing 1 × 10$^6$ cells were prepared by suitably diluting the cell suspension obtained in the primary culture with MEM-TPB-CS solution, and were placed in a dish and kept at 37° C in the same manner as in the primary culture. In this manner, the successive culture was carried out until the tertiary culture was obtained, and in each stage the number of viable cells in the cell suspension was measured.

As the result of these tests, it was proved that the number of viable cells in the cell suspension obtained by using the protease of this invention was always larger than that of viable cells obtained by using trypsin. The maximum number was obtained when the protease of this invention was employed at a concentration of 500 u/ml (see Table 2-1).

In the primary and successive cultures the number of live cells in the cell suspensions obtained by using trypsin to strip cells off the surface of the culture vessel was not always increased. Actually, in the primary and tertiary cultures, the number was decreased. Thus, the cultivation by trypsin was unstable. On the other hand, the number of viable cells in the cell suspensions obtained by using the protease of this invention steadily increased (see Tables 2-2, 2-3 and 2-4).

In Dulbecco's PBS solution, the number of cells obtained by using the protease of this invention was no less than that obtained by using trypsin.

Table 2-1

Dispersion of tissue pieces of the body of a chicken embryo by the use of the protease of this invention and trypsin

| Test No. | Treating Condition Enzyme employed to disperse tissue pieces | Concentration | Number of suspended viable cells obtained per chicken embryo |
|---|---|---|---|
| 1 | Trypsin | 0.125% | $6.7 \times 10^7$ |
| 2 | The protease of this invention | 1000 u/ml | $1.5 \times 10^8$ |
| 3 | " | 500 u/ml | $2.2 \times 10^8$ |
| 4 | " | 100 u/ml | $1.6 \times 10^8$ |
| 5 | " | 50 u/ml | $1.6 \times 10^8$ |

Table 2-2

Primary Culture

| Test No. | Treating Condition Enzyme employed | Concentration | Number of viable cells inoculated in a dish | Number of viable cells obtained after 4 day-culture |
|---|---|---|---|---|
| 1 | Trypsin | 0.125% | $5.0 \times 10^6$ | $4.5 \times 10^6$ |
| 2 | The protease of this invention | 1000 u/ml | $5.0 \times 10^6$ | $5.2 \times 10^6$ |
| 3 | " | 500 u/ml | $5.0 \times 10^6$ | $8.0 \times 10^6$ |
| 4 | " | 100 u/ml | $5.0 \times 10^6$ | $6.1 \times 10^6$ |
| 5 | " | 50 u/ml | $5.0 \times 10^6$ | $8.3 \times 10^6$ |

Table 2-3

Secondary Culture

| Test No. | Treating Condition Enzyme employed | Concentration | Number of viable cells inoculated in a dish | Number of viable cells obtained after 3-day-culture |
|---|---|---|---|---|
| 1 | Trypsin | 0.125% | $1.0 \times 10^6$ | $1.6 \times 10^6$ |
| 2 | The protease of this invention | 1000 u/ml | $1.0 \times 10^6$ | $1.3 \times 10^6$ |
| 3 | " | 50 u/ml | $1.0 \times 10^6$ | $1.7 \times 10^6$ |

Table 2-4

Tertiary Culture

| Test No. | Treating Condition Enzyme employed | Concentration | Number of viable cells inoculated in a dish | Number of viable cells obtained after 4 day-culture |
|---|---|---|---|---|
| 1 | Trypsin | 0.125% | $1.0 \times 10^6$ | $6.30 \times 10^5$ |
| 2 | The protease of this invention | 1000 u/ml | $1.0 \times 10^6$ | $1.25 \times 10^6$ |
| 3 | " | 50 u/ml | $1.0 \times 10^6$ | $1.25 \times 10^6$ |

EXAMPLE 3

Preparation of cell suspension from monolayer culture of mouse fibroblast of strain L-929

Before the treatment by the protease of this invention, L-cells were cultivated in a TD40 culture vessel containing MEM-FCS (9 : 1) as a culture medium, and the grown cells on the surface of the culture vessel were stripped off by a rubber cleaner to prepare a cell suspension. The thus prepared cell suspension was placed in short test tubes, and subjected to a stationary culture at 37° C to grow cells on the glass surface. After 2 days of culture, the culture medium in some of the test tubes was replaced by 1 ml of PBS or MEM-FCS (9 : 1) solution containing the protease of this invention, and the test tube was kept at 37° C. After a predetermined time, 0.2 ml of 0.4% erythrosine-PBS solution was put in the test tube, and the number of free viable cells in the test tube was measured by a hemacytometer. The total number of cells in the test tube was also measured by the crystal violet staining method to compare the number of free viable cells with that of the total number.

PBS solution containing trypsin at a concentratioin of about 200 u/ml has been heretofore used to disperse cells attached to the surface of a culture vessel, and so the trypsin was employed as a comparative control.

Figure 1:
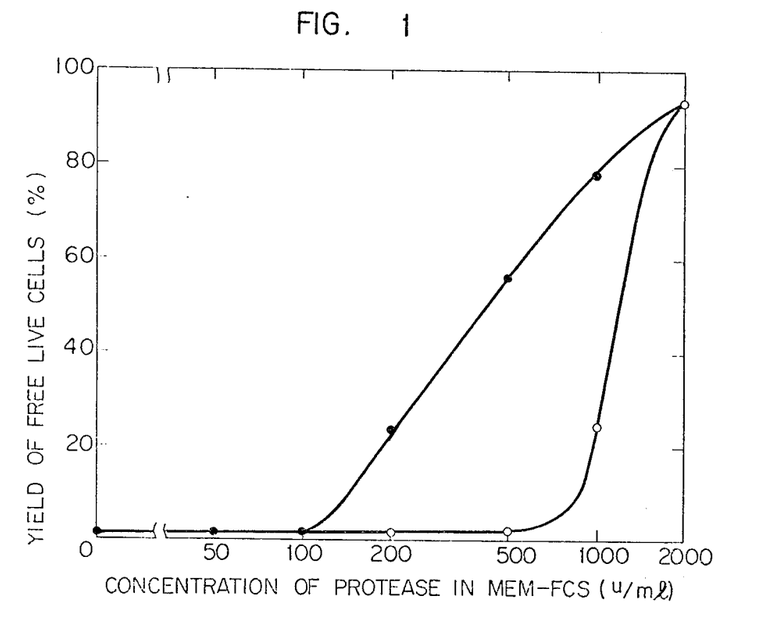
FIG. 1 shows yields of free viable L-929 cells (to the total number of cells) obtained by treating monolayer culture cells at 37° C for 10 minutes with MEM-FCS (9 : 1) solutions containing the protease of this invention (expressed by the curve •—• ) or trypsin (expressed by the curve o—o) at various concentrations.
Figure 2:
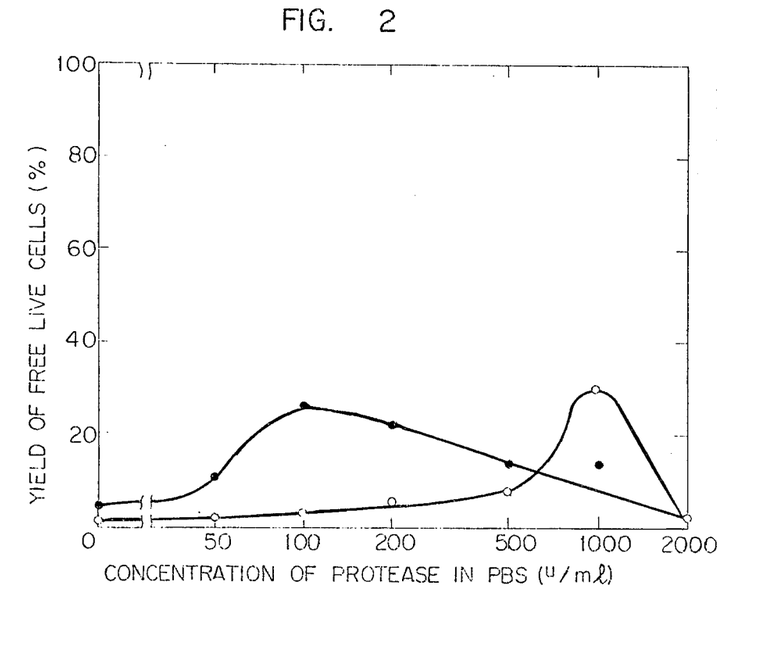
FIG. 2 shows yields of free viable cells obtained in the same manner as in FIG. 1, except that PBS is used in place of MEM-FCS as a medium.

PBS or MEM-FCS (9 : 1) solutions containing the protease of this invention at various concentrations in the range of 50 to 2,000 u/ml and PBS or MEM-FCS (9 : 1) solutions containing trypsin at various concentrations in the range of 50 to 2,000 u/ml were tested by treating monolayer culture cells for 10 minutes at 37° C. Yields of free viable cells obtained by the treatment with PBS solution containing the protease of this invention and the PBS solution containing trypsin were both 30% of the total even at their optimum protease concentration, while yields of free viable cells obtained by the treatment with MEM-FCS solution containing the protease of this invention and MEM-FCS solution containing trypsin were both approximately 100% (see FIGS. 1 and 2). As can be seen from FIG. 1, the yield of viable cells obtained by the treatment with MEM-FCS solution containing the protease of this invention gradually increases as the concentration of the protease increases, while the yield of viable cells by treatment with MEM-FCS solution containing trypsin at first remains low then rapidly increases as the concentration of trypsin increases.

Figure 3:
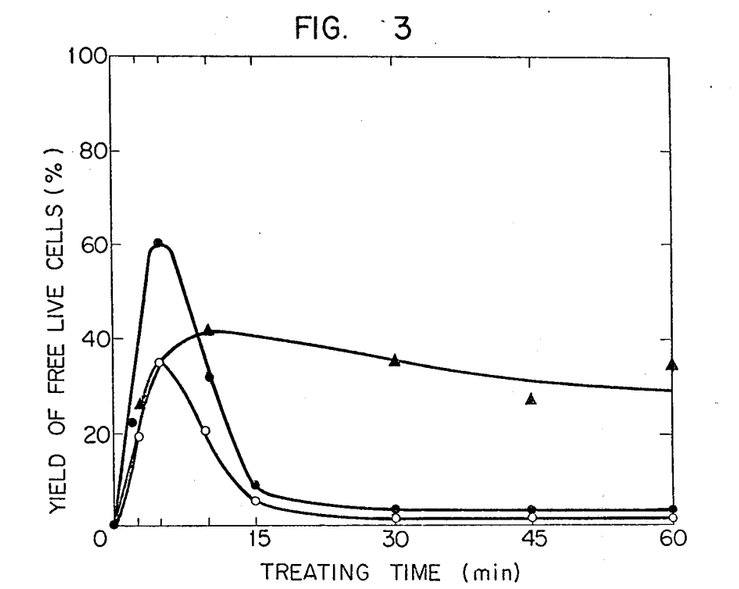
FIG. 3 shows the relationship between the treating time and the yield of free viable L-929 cells obtained by treating monolayer culture cells at 37° C for various periods of time with the PBS solution containing trypsin at various concentrations of 50 u/ml (expressed by the curve ▲—▲), 200 u/ml (expressed by the curve o—o) and 1,000 u/ml (expressed by the curve •—• ).
Figure 4:
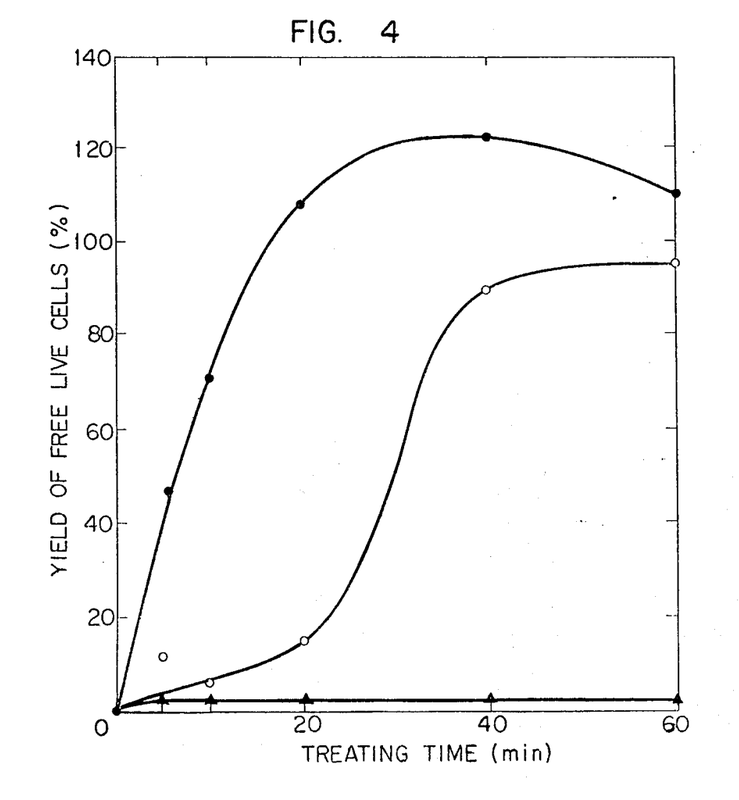
FIG. 4 shows the relationship between the treating time and the yield of free viable L-929 cells obtained by treating monolayer culture cells at 37° C for various periods of time with MEM-FCS (9 : 1) solution containing the protease of this invention at various concentrations of 50 u/ml (expressed by the curve ▲—▲), 200 u/ml (expressed by the curve o—o) and 1000 u/ml (expressed by the curve •—• ).

The relationship between the yield of free viable cells and the treating time (0 to 60 minutes) was studied by using MEM-FCS solution containing the protease of this invention at concentrations of 50 u/ml, 200 u/ml and 1,000 u/ml and PBS solution containing trypsin at concentrations of 50 u/ml, 200 u/ml and 1,000 u/ml. FIG. 3 shows the relationship between the treating time and the yield of free viable cells obtained by treating monolayer culture cells at 37° C with the PBS solution containing trypsin. FIG. 4 shows the relationship between the treating time and the yield of free live cells obtained by treating monolayer culture cells at 37° C with the MEM-FCS solution containing the protease of this invention. As can be seen from FIG. 3, the yield of free viable cells obtained by the treatment with the trypsin PBS solution reached a maximum within 10 minutes. When the treating time is extended further, the yield decreases rapidly. On the other hand, as can be seen from FIG. 4, when cells are treated with the MEM-FCS solution containing the protease of this invention at concentrations of 200 u/ml and 1,000 u/ml, almost all of the cells are recovered as free viable cells, and the yield of the free viable cells does not substantially decrease even when the treating time is extended longer. However it was proved that the MEM-FCS solution containing the protease of this invention at a concentration of 50 u/ml was not effective in stripping cells off the surface of the culture vessel during a 60 minutes trial, and the cells were not stripped off even after 48 hours.

In addition to the foetal calf serum, calf, bovine or equine serum could be equally added to MEM and such a protease solution comprising the above serum worked effectively in producing free viable cells.

The successive cultivation of the free viable cells obtained by treatment with the protease of this invention was effectively carried out by reducing the concentration of the protease to less than 50 u/ml by diluting the protease solution or centrifugally separating the protease solution from cells. In the successive culture the cells grew again on a surface of a culture vessel.

In conclusion, the yield of free viable cells obtained from L-cells attached to the surface of a culture vessel by treating them with the protease of this invention in a serum-containing medium is higher than that obtained by treatment with trypsin in PBS, and in the case of the protease of this invention it is easy to determine the optimum concentration and treating time.

EXAMPLE 4

Suspension culture of mouse fibroblasts of strain L-929

A cell suspension comprising L-cells and MEM-FCS (9 : 1) was prepared in the same manner as in Example 3. A culture medium comprising the prepared cell suspension and the protease of this invention was put in short test tubes in an amount of 1 ml, and was cultivated at 37° C for 2 days or 3 days, and the number of free live cells obtained and the total number of cells was measured in the same manner as in Example 3. In the successive culture operation, the test tube containing the cell suspension was subjected to a centrifuge at 700 rpm for 10 minutes to deposit the cells. The supernatant fluid was discarded with a pipette, and 1 ml of a fresh MEM-FCS solution containing the protease of this invention was added in the same test tube to be cultivated again at 37° C. The successive cultivation was continued by diluting the cell suspension with a fresh medium in a ratio of 1 to 1 or 1 to 2 when the number of cells increased.

Figure 61:
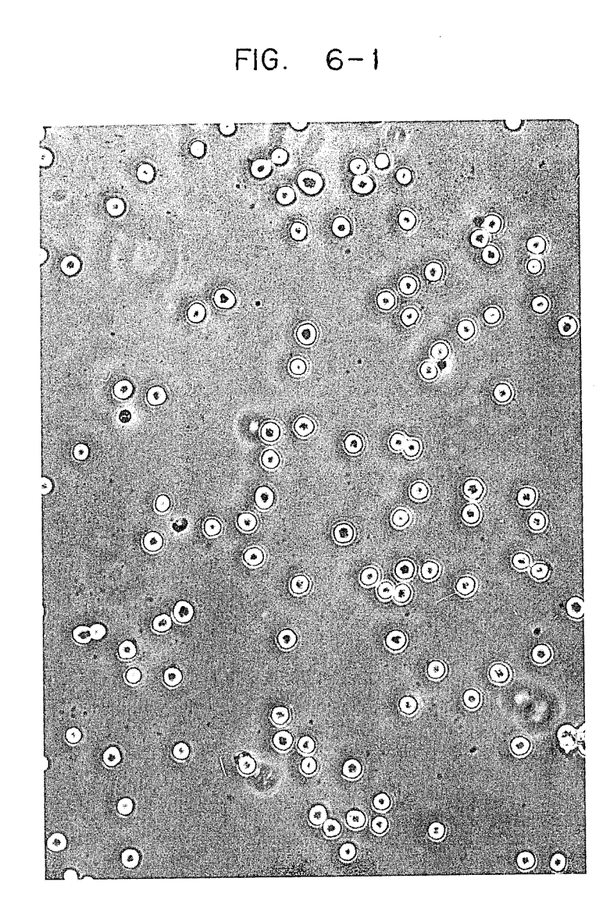
Figure 62:
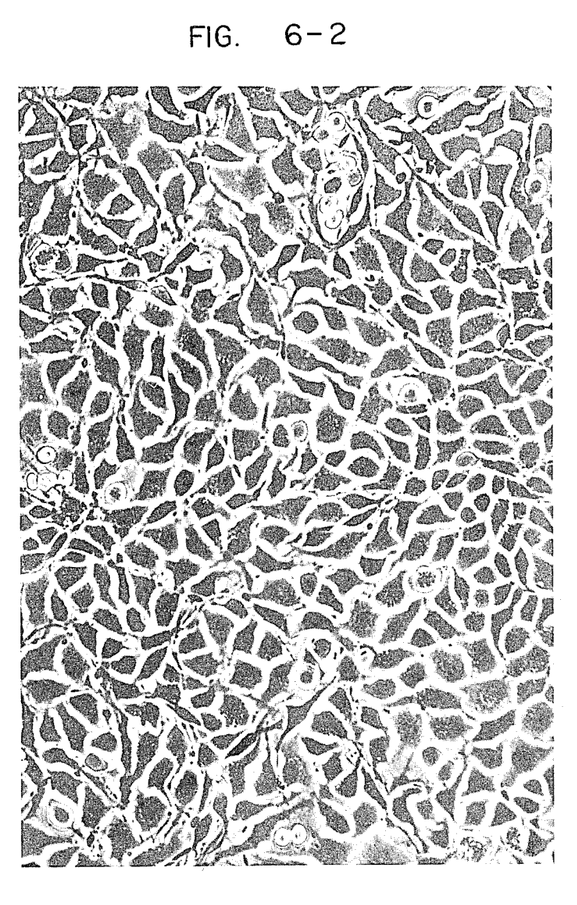

As can be seen from FIG. 6-1, in a culture medium containing the protease of this invention, cells grow in a dispersed state, while in a culture medium containing no protease of this invention, cells grow in a state of being attached on glass surfaces (see FIG. 6-2).

Figure 5:
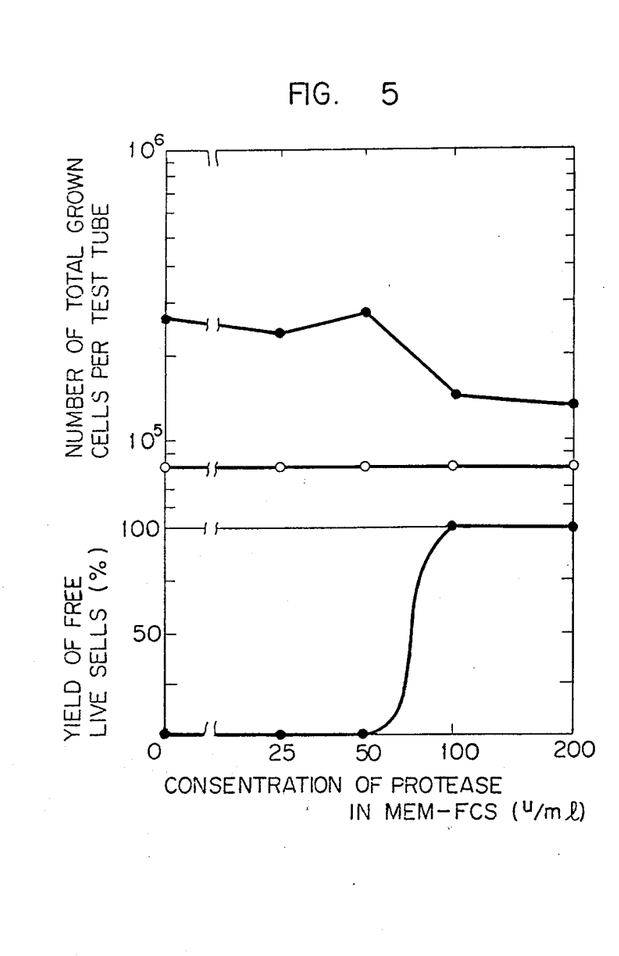
FIG. 5 shows the total number of cells per test tube (expressed by the curve •—• ) and the yield of free viable cells (expressed by the curve •—• ) obtained by a stationary suspension culture at 37° C for 2 days in MEM-FCS solution containing the protease of this invention at various concentrations. The curve o—o shows the number of cells originally added in the test tube.

As can be seen from FIG. 5, the yields of free viable cells obtained by treating the cells for 2 days with MEM-FCS solution containing the protease of this invention at concentrations of 100 u/ml and 200 u/ml were respectively 103% and 101% of the total cells, and substantially no cells were attached to the glass surface (see FIG. 6-1). On the other hand, the yields of free viable cells obtained by the treatment with the protease of this invention at concentrations of 25 u/ml and 50 u/ml were less than 2%. The yield of free viable cells obtained by using a culture medium containing no protease was also less than 2%.

Figure 7:
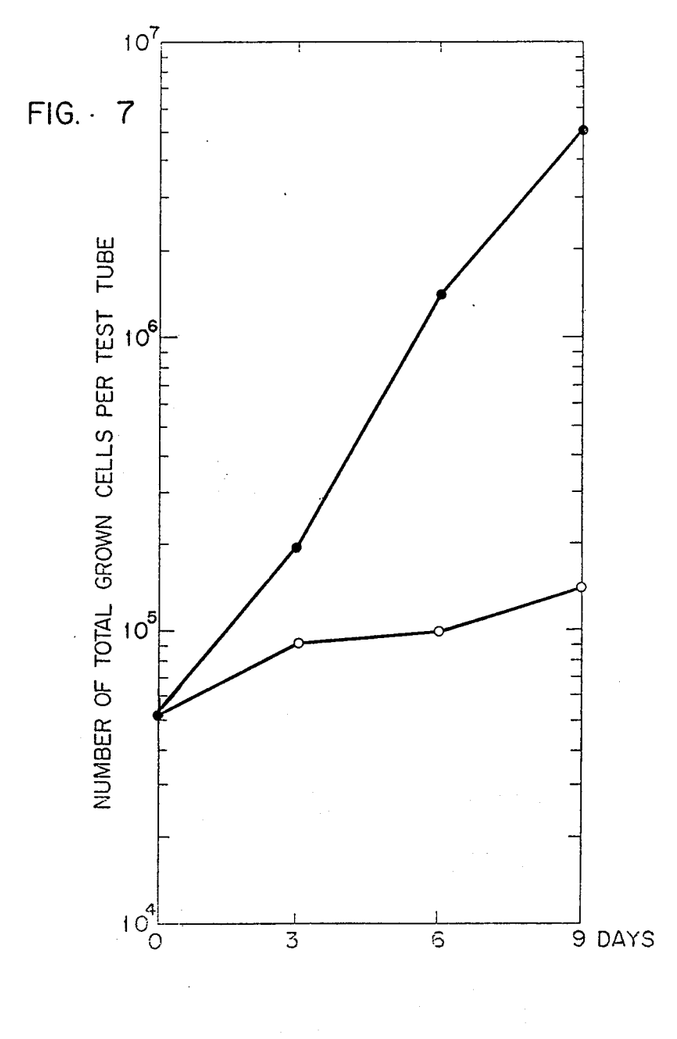
FIG. 7 shows growth curves of L-929 cells obtained by a stationary suspension culture at 37° C respectively in MEM-FCS (9 : 1) solution containing the protease of this invention at concentration of 200 u/ml (expressed by the curve o—o) and in MEM-FCS (9 : 1) solution containing no protease (expressed by the curve •—• ). In both cases, the culture medium was renewed on every third day.

The growth of L-cells in a state of suspension in MEM-FCS (9 : 1) solution containing the protease of this invention according to suspension culture method was measured. As a control, the growth of L-cells in the same medium containing no protease according to replicate culture method was measured. As can be seen from FIG. 7, although the growth in the suspension culture using the protease of this invention was a little inhibited in comparison with that in the monolayer culture using no protease, the growth steadily increased.

Figure 8:
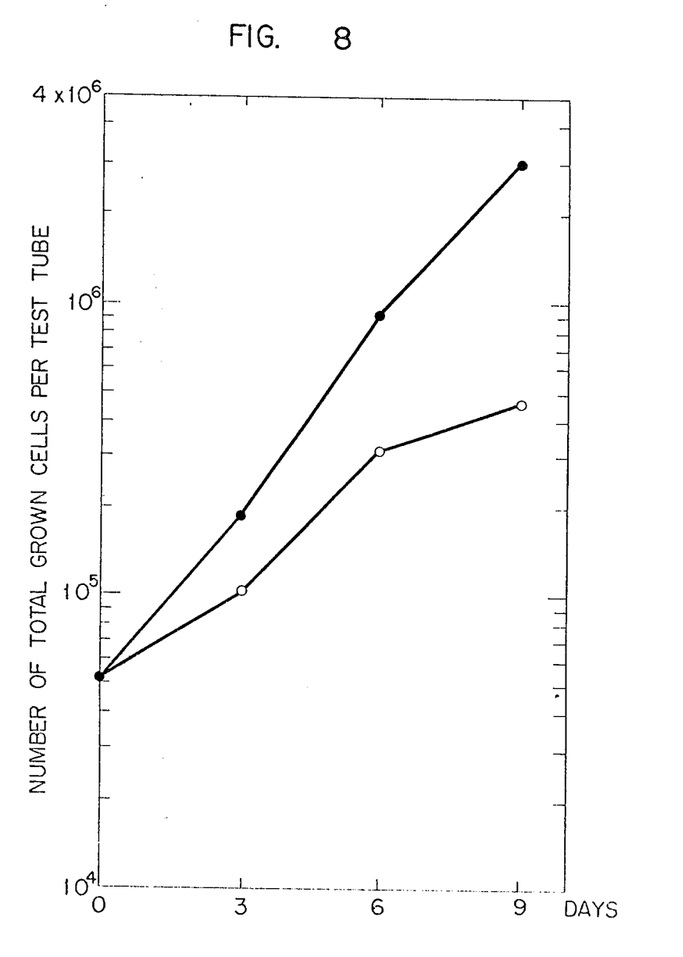
FIG. 8 shows growth curves of L-S$_2$ cells obtained by a stationary suspension culture at 37° C respectively in MEM-FCS (9 : 1) solution containing the protease of this invention at a concentration of 200 u/ml (expressed by the curve o—o) and in MEM-FCS (9 : 1) solution containing no protease (expressed by the curve •—• ). In both cases, the culture medium was renewed on every third day.

When the suspension culture was continued for one month in a culture medium containing 200 u/ml of the protease of this invention, a substrain was developed and was referred to as L-S$_2$. Growth curves of the above substrain (L-S$_2$) after four months-suspension culture were shown in FIG. 8. When L-S$_2$ cells were placed in a culture medium without containing the protease of this invention, they grew on a glass surface of the culture vessel, attaching thereto.

As mentioned above, in a culture medium containing the protease of this invention and serum, it was possible to carry out suspension culture and to grow without stirring or agitating.

What we claim is: )

1. A method for dispersing animal tissue, which comprises admixing the animal tissue with a neutral protease having the following characteristics:
 a. optimum pH of 8.5 for proteolytic activity to casein,
 b. stable within a pH range of 4–9,
 c. active within a temperature range of 20°–75° C, with the optimum temperature being 60° C,
 d. absence of activity at pH below 3 and pH above 10, and absence of activity upon heating at 65° C for 10 minutes,
 e. activity inhibited by ethylenediaminetetraacetate, citric acid, o-phenanthroline, 2,2′-dipyridyl, sodium fluoride, N-bromosuccinimide and iodine,
 f. activity enhanced by $Ca^{++}$, $Mn^{++}$, $Mg^{++}$, $Fe^{++}$, $Fe^{+++}$ to and $Al^{+++}$, g. molecular weight of 35,900 as determined by ultracentrifugal analysis, h. elemental analysis of 46.57% C, 7.17% H, 31.57% O, 14.48% N and 0.21% S, and i. cleaves the peptide bonds in the oxidized B-chain of insulin at positions Phe(1)-Val(2), His(5)-Leu(6), His(10)-Leu(11), Glu(13)-Ala(14), Ala(14)-Leu(15), Leu(15)-Tyr(16), Tyr(16)-Leu(17), Leu(17)-Val(18), Gly(23)-Phe(24), Phe(24)-Phe(25), Phe(25)-Tyr(26) and Lys(29)-Ala(30).

2. A method for dispersing animal tissue culture cells, which comprises admixing the culture cells with a neutral protease having the following characteristics:

a. optimum pH of 8.5 for proteolytic activity to casein, b. stable within a pH range of 4–9, c. active within a temperature range of 20°–75° C, with the optimum temperature being 60° C, d. absence of activity at pH below 3 and pH above 10, and absence of activity upon heating at 65° C for 10 minutes, e. activity inhibited by ethylenediaminetetraacetate, citric acid, o-phenanthroline, 2,2'-dipyridyl, sodium fluoride, N-bromosuccinimide and iodine, f. activity enhanced by $Ca^{++}$, $Mn^{++}$, $Mg^{++}$, $Fe^{++}$, $Fe^{+++}$ and $Al^{+++}$, g. molecular weight of 35,900 as determined by ultracentrifugal analysis, h. elemental analysis of 46.57% C, 7.17% H, 31.57% O, 14.48% N and 0.21% S, and i. cleaves the peptide bonds in the oxidized B-chain of insulin at positions Phe(1)-Val(2), His(5)-Leu(6), His(10)-Leu(11), Glu(13)-Ala(14), Ala(14)-Leu(15), Leu(15)-Tyr(16), Tyr(16)-Leu(17), Leu(17)-Val(18), Gly(23)-Phe(24), Phe(24)-Phe(25), Phe(25)-Tyr(26) and Lys(29)-Ala(30).

3. In a method for culturing animal tissue cells, which comprises suspending the cells in a serum-containing medium, the improvement wherein the serum-containing medium contains a neutral protease having the following characteristics:

a. optimum pH of 8.5 for proteolytic activity to casein, b. stable within a pH range of 4–9, c. active within a temperature range of 20°–75° C, with the optimum temperature being 60° C, d. absence of activity at pH below 3 and pH above 10, and absence of activity upon heating at 65° C for 10 minutes, e. activity inhibited by ethylenediaminetetraacetate, citric acid, o-phenanthroline, 2,2'-dipyridyl, sodium fluoride, N-bromosuccinimide and iodine, f. activity enhanced by $Ca^{++}$, $Mn^{++}$, $Mg^{++}$, $Fe^{++}$, $Fe^{+++}$ and $Al^{+++}$, g. molecular weight of 35,900 as determined by ultracentrifugal analysis, h. elemental analysis of 46.57% C, 7.17% H, 31.57% O, 14.48% N and 0.21% S, and i. cleaves the peptide bonds in the oxidized B-chain of insulin at positions Phe(1)-Val(2), His(5)-Leu(6), His(10)-Leu(11), Glu(13)-Ala(14), Ala(14)-Leu(15), Leu(15)-Tyr(16), Tyr(16)-Leu(17), Leu(17)-Val(18), Gly(23)-Phe(24), Phe(24)-Phe(25), Phe(25)-Tyr(26) and Lys(29)-Ala(30).

* * * * *